(12) United States Patent
Ninomiya et al.

(10) Patent No.: US 7,605,180 B2
(45) Date of Patent: Oct. 20, 2009

(54) NATEGLINIDE-CONTAINING PREPARATION

(75) Inventors: Nobutaka Ninomiya, Kawasaki (JP); Chisato Makino, Kawasaki (JP); Akira Yabuki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/421,898

(22) Filed: Apr. 24, 2003

(65) Prior Publication Data

US 2004/0014815 A1 Jan. 22, 2004

Related U.S. Application Data

(63) Continuation of application No. PCT/JP01/09291, filed on Oct. 23, 2001.

(30) Foreign Application Priority Data

Oct. 24, 2000 (JP) ............................. 2000-324373

(51) Int. Cl.
*A61K 31/195* (2006.01)
*C07C 229/00* (2006.01)

(52) U.S. Cl. ...................................... 514/563; 562/450

(58) Field of Classification Search ................. 562/450; 514/563
See application file for complete search history.

(56) References Cited

U.S. PATENT DOCUMENTS

| | | | |
|---|---|---|---|
| 5,463,116 A | 10/1995 | Sumikawa et al. | |
| 5,488,150 A | 1/1996 | Sumikawa et al. | |
| 6,143,323 A | 11/2000 | Yabuki et al. | 424/464 |
| 6,296,872 B1 | 10/2001 | Yabuki et al. | 424/464 |
| 6,641,841 B2 | 11/2003 | Yabuki et al. | 424/480 |
| 2003/0021843 A1 | 1/2003 | Makino et al. | |
| 2003/0073729 A1 | 4/2003 | Kitahara et al. | |
| 2003/0147951 A1 | 8/2003 | Yabuki et al. | |
| 2003/0229249 A1 | 12/2003 | Sumikawa et al. | |
| 2004/0002544 A1 | 1/2004 | Makino et al. | |
| 2004/0024219 A1 | 2/2004 | Sumikawa et al. | |
| 2004/0029968 A1 | 2/2004 | Ninomiya et al. | 514/563 |
| 2004/0030182 A1 | 2/2004 | Takahashi et al. | |

FOREIGN PATENT DOCUMENTS

| | | |
|---|---|---|
| CN | 1242704 A | 1/2000 |
| EP | 0 526 171 A2 | 2/1993 |
| EP | 0 965 339 A1 | 12/1999 |
| JP | 4-15221 | 3/1992 |
| JP | 05-208943 | 8/1993 |
| JP | 2508949 | 4/1996 |
| JP | 10-194969 | 7/1998 |
| WO | WO98/22105 | 5/1998 |

OTHER PUBLICATIONS

U.S. Appl. No. 11/246,453, filed Oct. 11, 2005, Makino, et al.
U.S. Appl. No. 11/319,177, filed Dec. 28, 2005, Sumikawa, et al.
U.S. Appl. No. 11/349,225, filed Feb. 8, 2006, Makino, et al.
Imaizumi, H., et al., "Stabilization of Amorphous State of Indomethacin by Solid Dispersion in Polyvinylpolypyrrolidone [1]," Chem. Pharm. Bull., vol. 31, No. 7, 1983, pp. 2510-2512.
Hirasawa, N., et al., "Stability of Nilvadipine Solid Dispersion Tablet with Non-Packaging Condition," Yakugaku Zasshi, vol. 124, No. 1, 2004, pp. 19-23, with partial English translation.

*Primary Examiner*—Taylor Victor Oh
(74) *Attorney, Agent, or Firm*—Oblon, Spivak, McClelland, Maier & Neustadt, L.L.P.

(57) ABSTRACT

The present invention discloses, as a immediate-release preparation useful as an antidiabetic, a nateglinide-containing preparation comprising nateglinide as an active ingredient wherein the nateglinide is amorphous.

20 Claims, 9 Drawing Sheets

NATEGLINIDE-CONTAINING PREPARATION

CROSS REFERENCES TO RELATED APPLICATIONS

This application is a continuation of International Patent Application No. PCT/JP01/09291, filed on Oct. 23, 2001, and claims priority to Japanese Patent Application No. 2000-324373, filed on Oct. 24, 2000, both of which are incorporated herein by reference in their entireties.

TECHNICAL FIELD OF THE INVENTION

The present invention relates to a preparation of nateglinide that is useful as an antidiabetic and more specifically to a immediate-release preparation of nateglinide.

BACKGROUND ART

It is known that nateglinide [compound name: N-(trans-4-isopropylcyclohexylcarbonyl)-D-phenylalanine] exhibits an excellent blood glucose-lowering effect by oral administration and therefore, is useful as a therapeutic agent for diabetes (Japanese Patent Publication No. Hei 4-15221).

On the other hand, the nateglinide is a poorly water soluble substance and therefore, capsules filled with nateglinide drug substance powder or ordinary tablets containing nateglinide do not dissolve well when administered orally because of its low disintegrating ability. As a result, such nateglinide-containing preparations can not show the fast-acting and short duration effect in decreasing a blood glucose level (fast-acting hypoglycemic agent), which is characteristic of nateglinide. In order to show the characteristic efficacy of nateglinide, the drug needs to be released rapidly from preparations and so improvement on a preparation has been required.

As methods for solving the problem, there has been provided a preparation wherein a low-substituted hydroxypropylcellulose is incorporated as a disintegrant (Japanese Patent No. 2508949).

Meanwhile, nateglinide has crystal polymorphs. Such a method wherein the disintegrant is incorporated into the preparation effectively enhance in disintegrating ability and increase in the dissolution rate of the preparation containing nateglinide in stable H-type crystal form and semi-stable crystal form. However, it can not be regarded as effective in all crystal forms of nateglinide.

Besides, when the nateglinide in crystal forms other than the most stable H-type crystal forms and the semi-stable crystal forms are used, it is known that crystal transition happens during producing or conserving preparations. It is generally preferred that crystal transition of drugs does not happen during producing or conserving pharmaceutical preparations.

DISCLOSURE OF THE INVENTION

An object of the present invention is to provide, as a nateglinide-containing preparation, a pharmaceutical preparation containing amorphous nateglinide wherein dissolution rate of drugs is high and crystal transition does not happen during producing or conserving preparations.

For the purpose of solving the problems, the inventors have vigorously studied and found that dissolution property can be improved by making nateglinide amorphous in a preparation and the like. The present invention has been completed on the basis of this finding. According to the method of the present invention, it is possible to provide, from nateglinide in any crystal polymorphs, an immediate-release preparation of nateglinide wherein dissolution rate of drugs is high and crystal transition does not happen during producing or conserving preparations. The present invention basically relates to a nateglinide-containing preparation as an active ingredient, wherein the nateglinide is amorphous. The present invention includes the following each invention:

(1) A nateglinide-containing preparation comprising nateglinide as an active ingredient wherein the nateglinide is amorphous.
(2) The nateglinide-containing preparation according to (1), wherein the amorphous nateglinide is produced by a solvent removal process from a solution of nateglinide in a solvent.
(3) The nateglinide-containing preparation according to (2), wherein the solvent used in the solvent removal process is a mixture of ethanol and water.
(4) The nateglinide-containing preparation according to (1), wherein the amorphous nateglinide is produced by applying a high shear stress.
(5) The nateglinide-containing preparation according to (1), wherein the amorphous nateglinide is produced by melt granulation process.
(6) The nateglinide-containing preparation according to (2), which comprises hydrophilic materials as carriers.
(7) The nateglinide-containing preparation according to (6), wherein the hydrophilic materials are selected from the group consisting of water-soluble polymers, water-swelling polymers, sugar alcohols and salts.
(8) The nateglinide-containing preparation according to (7), wherein the water-soluble polymers or the water-swelling polymers are selected from the group consisting of polyvinyl pyrrolidone derivatives, polysaccharide derivatives, polyacrylic acid derivatives, polylactic acid derivatives, polyoxyethylene derivatives, polyvinyl alcohol derivatives and surfactants.
(9) The nateglinide-containing preparation according to (8), wherein the polysaccharide derivatives are selected from the group consisting of methylcellulose SM-4, hydroxypropylcellulose SL and hydroxypropylcellulose SSL.
(10) The nateglinide-containing preparation according to (8), wherein the polyoxyethylene derivatives are polyethyleneglycol.
(11) The nateglinide-containing preparation according to (7), wherein the sugar alcohols is selected from the group consisting of sorbitol, xylitol and mannitol.
The nateglinide-containing preparation according to (7), wherein the water-swelling polymers are crospovidone (KOLLIDON CL-M).
(13) The nateglinide-containing preparation according to (1), wherein the preparation is a tablet containing the amorphous nateglinide.
(14) The nateglinide-containing preparation according to (1), wherein the product is a capsule filled with liquid in which nateglinide is dissolved.
(15) The nateglinide-containing preparation according to (14), wherein the liquid in which nateglinide is dissolved is either water-soluble polymers or surfactants.
(16) The nateglinide-containing preparation according to (15), wherein the water-soluble polymers or the surfactants dissolving nateglinide are polyoxyethylene derivatives.
(17) A method for producing an amorphous nateglinide-containing preparation, which comprises the steps of dissolving nateglinide crystals into a pharmacologically acceptable solvent together with hydrophilic materials selected from the group consisting of water-soluble polymers, water-swelling polymers, sugar alcohols and salts, and subjecting the resulting solution to a process selected from the group consisting of a fluidized bed granulation process, a high-speed mixing granulation process, a spray-dry process and a coating process to granulate the amorphous nateglinide.

(18) A method for producing an amorphous nateglinide-containing preparation, which comprises the steps of mixing nateglinide crystals with hydrophilic materials selected from the group consisting of water-soluble polymers, water-swelling polymers, sugar alcohols and salts, and then applying a shear stress to the resulting mixture.

(19) A method for producing an amorphous nateglinide-containing preparation, which comprises the steps of mixing nateglinide crystals with hydrophilic materials selected from the group consisting of water-soluble polymers, water-swelling polymers, sugar alcohols and salts, and then subjecting the resulting mixture to a melt-kneading with heating and grinding with cooling.

(20) A method for producing an amorphous nateglinide-containing preparation, which comprises the step of dissolving nateglinide crystals into pharmacologically acceptable liquid additives.

BEST MODE FOR CARRYING OUT THE INVENTION

Figure 1:
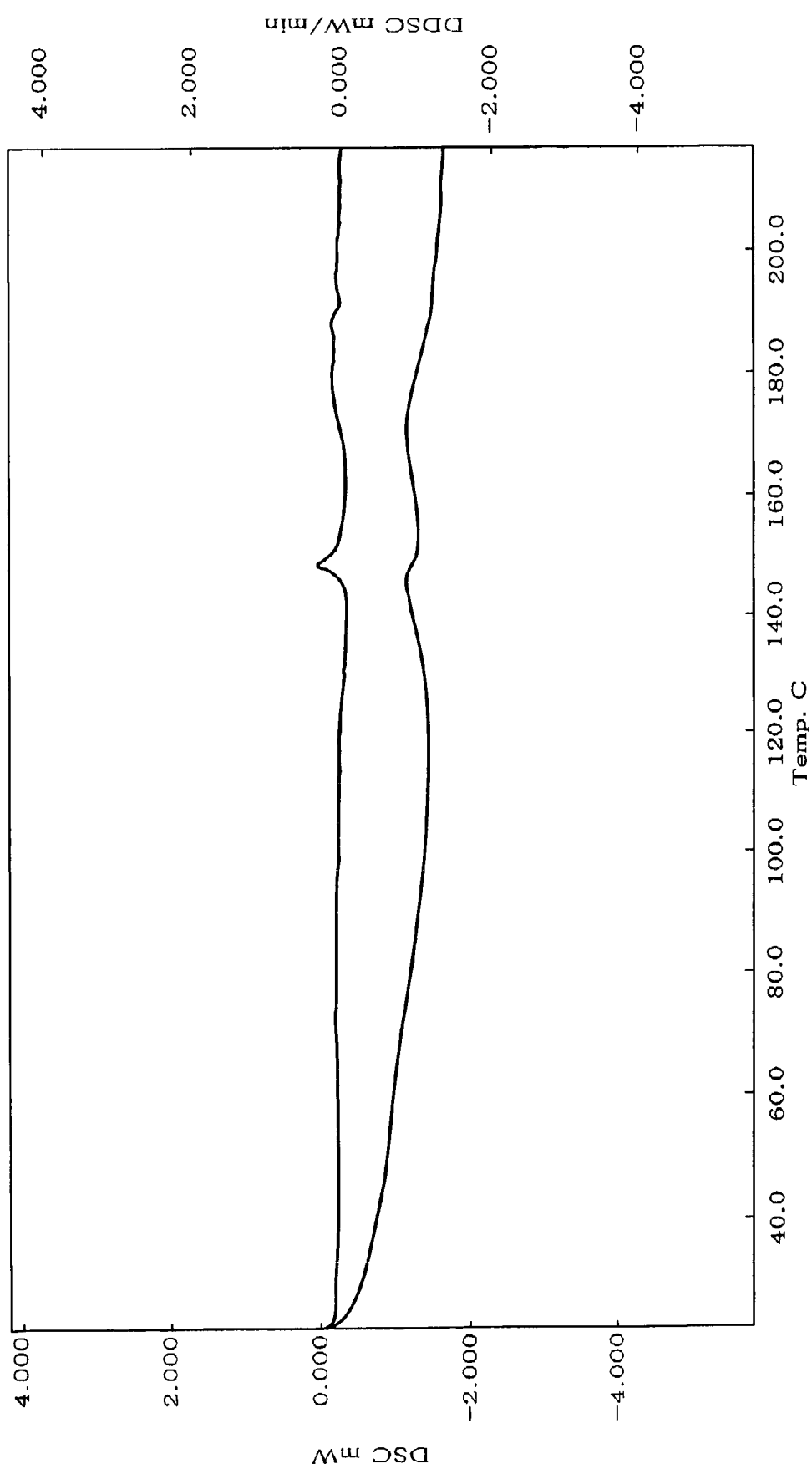
FIG. 1 shows a DSC pattern of amorphous nateglinide tablets.

Nateglinide, which is a raw material of amorphous nateglinide that is contained in the pharmaceutical preparation of the present invention may be synthesized by the method described in, for example, Japanese Patent, Publication No. Hei 4-15221, and the crystal forms thereof are not particularly limited.

Preparation methods for amorphous nateglinide include, for example, a solvent removal process, a process applying a high shear stress, a melt granulation process, and a process dissolving into a pharmaceutically acceptable solvent. Other methods are also acceptable if only it can make nateglinide amorphous. Among these methods, the solvent removal process and the process dissolving into a pharmaceutically acceptable solvent are preferable in view of easy-producibility and the like. Making amorphous state can be accomplished without a carrier.

A hydrophilic material is preferable as a carrier that makes nateglinide amorphous. Examples thereof include water-soluble polymers, water-swelling polymers, sugar alcohols and salts. Carriers may be any of those which can make nateglinide amorphous and dissolve or swell rapidly in water. The addition amount is preferably 0.1 or more by weight to drugs. It is more preferably 0.1 to 100 by weight and further more preferably 0.1 to 50 by weight to nateglinide.

A solvent for dissolving nateglinide is preferably a pharmaceutically acceptable liquid at about 37° C. Examples thereof are water-soluble polymers and surfactants. The solvent is added preferably 0.1 or more by weight to drugs. It is more preferably 0.1 to 1000 by weight to nateglinide and further more preferably 0.1 to 100 by weight to nateglinide. It is preferably 0 to 100 by weight and more preferably 0 to 50 by weight to a carrier that makes nateglinide amorphous.

The solvent removal process for obtaining amorphous nateglinide used in the pharmaceutical preparations of the present invention is a method wherein drugs and a carrier for making amorphous state are dissolved into a solvent, and then the solvent is removed to make the drugs amorphous. The solvent may be any of an aqueous type, an organic type and a mixed type of water and an organic solvent, as long as drugs and the carrier can be dissolved thereinto. Concretely, it includes alcohols such as methanol, ethanol and isopropyl alcohol, ketones such as acetone and methylethyl ketone, cyclic ethers such as dioxane and tetrahydrofuran, and acetonitrile. Ethanol is preferred among them. When the mixed type of water and an organic solvent is used, their ratio (mass ratio) is preferably water: an organic solvent=99:1 to 1:99 and more preferably 90:10 to 10:90.

An example of the solvent removal process includes a method wherein drugs and a carrier that make nateglinide amorphous such as water-soluble polymers are dissolved into a solvent such as ethanol, and then the solution is subjected to drying under vacuum, evaporation and the like to remove the solvent. Conditions of removal of the solvent are not particularly limited as long as amorphous nateglinide can exist stably. The operation can be conducted by using nateglinide and the solvent without a carrier for making amorphous state. The amorphous nateglinide may be subjected to a fluidized-bed granulation process, a high-speed mixing granulation process, a spray-dry process, a coating process and the like to obtain granules containing amorphous nateglinide. Without removing the solvents from the solution into which nateglinide and the carrier that makes nateglinide amorphous are dissolved, the solution may be directly subjected to the fluidized-bed granulation process, the high-speed mixing granulation process, the spray-dry process, the coating process and the like to directly obtain a granulated nateglinide-containing preparation. Conditions of the fluidized-bed granulation and the like are not particularly limited as long as amorphous nateglinide can exist stably. The operation can be conducted by nateglinide alone. The obtained granules can be utilized as dosage form, granules, or further be compressed to tablets. Dosage forms of the nateglinide-containing preparation of the present invention are not particularly limited.

The method for producing preparations by applying a high shear stress is the method wherein a high shear stress is applied to the mixture of drugs and a carrier for making amorphous state by an appropriate method to make the drugs amorphous. The applied shear stress is not particularly limited as long as amorphous nateglinide can exist stably. The operation can be conducted by nateglinide alone.

For example, there is a method wherein drugs and water-soluble polymers are mixed, and then the mixture is coground with an ultracentrifugal mill, or a high shear stress is applied to the mixture by an extrusion granulator, to obtain granules containing the amorphous drugs. The obtained granules can be utilized as dosage form, granules, or further be compressed to tablets. Dosage forms of the nateglinide-containing preparation of the present invention are not particularly limited.

The melt granulation process is the method wherein the mixture of drugs and a carrier for making amorphous state is heated and melted and then it is cooled and solidified to make the drugs amorphous.

For example, drugs and water-soluble polymers are placed in a heat-resistant multi-purpose mixer or the like, melt-kneaded with heating, and ground with cooling to obtain granules containing the amorphous drugs. The obtained granules can be utilized as dosage form, granules, or, insofar as an amorphous state is maintained, dosage forms of the nateglinide-containing preparation of the present invention are not particularly limited. The operation can be conducted by nateglinide alone.

The method dissolving into a pharmaceutically acceptable liquid additives is the method wherein drugs are dissolved into a pharmaceutically acceptable liquid additive to make the drugs amorphous.

For example, there may be a method wherein drugs are dissolved into water-soluble polymers that is liquid at 37° C. to obtain a solution. The solution is filled in a hard capsule shell, or it is filled in a soft capsule shell to be a liquid-filled capsule.

The preparation containing amorphous nateglinide of the present invention can further comprise hydrophilic materials. The hydrophilic materials include water-soluble polymers, water-swelling polymers, sugar alcohols, salts and the like. As such hydrophilic materials, the same one can be used as the carrier that makes nateglinide amorphous or a different materials can also be used.

Examples of water-soluble polymers or water-swelling polymers are polyvinyl pyrrolidone derivatives, polysaccharide derivatives, polyacrylic acids derivatives, polylactic acids derivatives, polyoxyethylene derivatives, polyvinyl alcohol derivatives and surfactants.

The polyvinyl pyrrolidone derivatives include cross-linked polyvinyl pyrrolidone and more concretely crospovidone (KOLLIDON CL-M, BASF).

The polysaccharide derivatives as the hydrophilic materials include cellulose derivatives and the like. Examples thereof are methylcellulose, hydroxypropylcellulose and carboxymethylcellulose. More concretely, it includes methylcellulose SM-4, hydroxypropylcellulose SL and hydroxypropylcellulose SSL.

The polyacrylic acids derivatives include methacrylic acid copolymer L, methacrylic acid copolymer S and methacrylic acid copolymer LD (Rohm)

The polylactic acids derivatives include copolymer of lactic acid and glycolic acid (1:1) having a molecular weight of 17000 to 24000.

As an example of the polyoxyethylene derivatives, polyethylene glycol is preferred. Particularly, its molecular weight is preferably 200 to 20000 and more preferably 200 to 6000. Concretely, it includes macrogol 300, 400, 600, 1000, 1500, 4000, 6000 or the like.

The polyvinyl alcohol derivatives include polyvinyl alcohols (completely saponified matters), polyvinyl alcohols (partially saponified matters) and the like.

The surfactants include polysorbate 80, sodium lauryl sulfate and the like.

As the water-swelling polymers, crospovidone (KOLLIDON CL-M) is preferred.

Sugar alcohols include sorbitol, xylitol, mannitol and the like. Mannitol is preferred among them.

The salts include sodium chloride, phosphates, citrates and the like.

EXAMPLES

The following Examples will further illustrate the present invention, which by no means limit the invention.

Example 1

Production of Amorphous Nateglinide 4 g of nateglinide in B-type crystal form and 32 g of polyvinyl pyrrolidone were dissolved into ethanol. Ethanol was removed by evaporation (60° C.), and the mixture was dried under vacuum at 60° C. for 3 hours or more. The solid material was ground in a mortar to obtain 36 g of nateglinide in the form of solid dispersion.

Examples 2

Production of Tablets Containing Amorphous Nateglinide 60 g of nateglinide (B-type crystals), 4 g of hydroxypropylcellulose and 60 g of crospovidone (KOLLIDON CL-M, BASF) were dissolved and suspended into 160 g of ethanol to obtain a binder solution. 180 g of crospovidone KOLLIDON CL-M, BASF) and 96 g of crystalline cellulose were placed in a fluidized bed granulator (FLO-1 type, Freund Industrial Co., Ltd.) and mixed together. Then the binder solution was sprayed to granulate into a fluidized bed (intake temperature: 80° C., spray speed: 4.9 g/min., spray pressure: 1.8 kgf/cm$^2$).

250 g of the obtained granules and 3.8 g of magnesium stearate were mixed in a V-type mixer to obtain granules for tabletting. A rotary tabletting machine (HT-AP15-ssII, Hata Factory) was used with a punch of 8 mm φ-14R2r to obtain 253.8 g of core tablets (weight of the core tablet: 203.1 mg).

80 g of hydroxypropylmethylcellulose, 15 g of macrogol 6000, 24 g of talc and 5 g of titanium oxide were dissolved and suspended into 876 g of water to prepare a liquid for coating. 300 g of the core tablets were placed in a tablet coater ("High Coater Mini", Freund Industrial Co., Ltd.). The tablets were coated so that 2.54 mg of hydroxypropylmethylcellulose is coated on one core tablet, to obtain 303.8 g of coated tablets.

The produced tablets was packed in an aluminum bag and stability test was conducted at 50° C. for one week or at 40° C., 75%RH, for one month.

Example 3

Production of Liquid-Filled Capsules 186 mg of nateglinide, 1456 mg of macrogol 400 and 1456 mg of polysorbate 80 were mixed in a stirrer at room temperature until they were dissolved and a transparent solution of nateglinide was prepared. 500 mg of the drug solution was filled in size 0 capsules to obtain liquid-filled capsules (nateglinide: 30 mg).

Comparative Example 1

Production of a Capsule 1 Filled with Drug Substance Powder 300 mg of nateglinide drug substance powder (B-type crystals) was filled in a gelatin capsule (size 2) to obtain a capsule filled with nateglinide drug substance powder in B-type form.

Comparative Example 2

Production of a Capsule 2 Filled with Drug Substance Powder 30 mg of nateglinide drug substance powder (H-type crystals) was filled in a gelatin capsule (size 2) to obtain a capsule filled with nateglinide drug substance powder in H-type form.

Comparative Example 3

Production of Tablets by Using Nateglinide in H-Type Crystals

A core tablet (weight: 120 mg) of 7 mm φ-9R2r was obtained by using nateglinide (H-type crystals) according to Example 1 of Japanese Patent Publication No. Hei 10-194969. Then it was coated to obtain a coated tablet containing nateglinide in H-type crystals.

Example 4

Measurement of DSC

Figure 2:
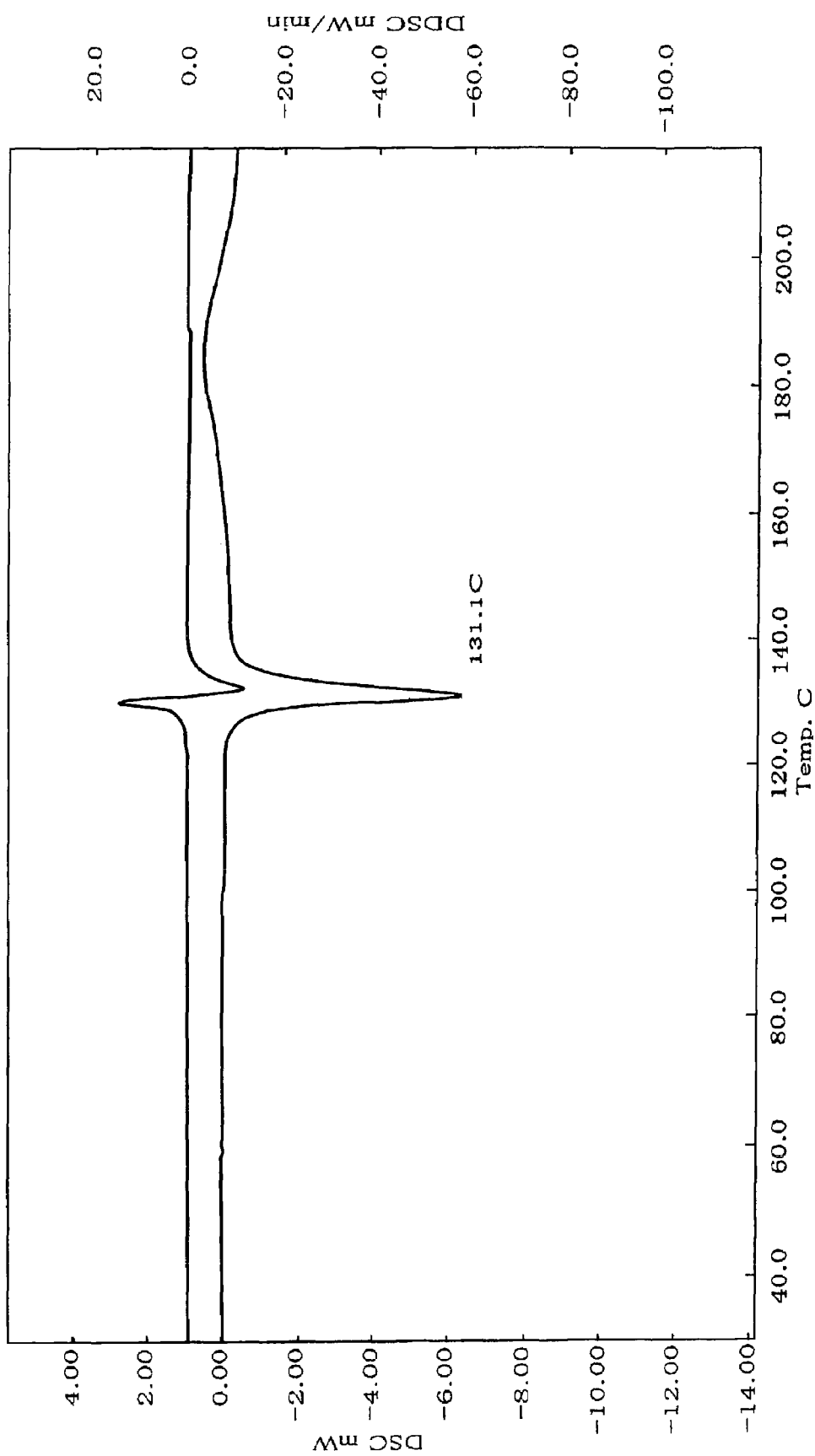
FIG. 2 shows a DSC pattern of B-type crystal form of a nateglinide drug substance.
Figure 3:
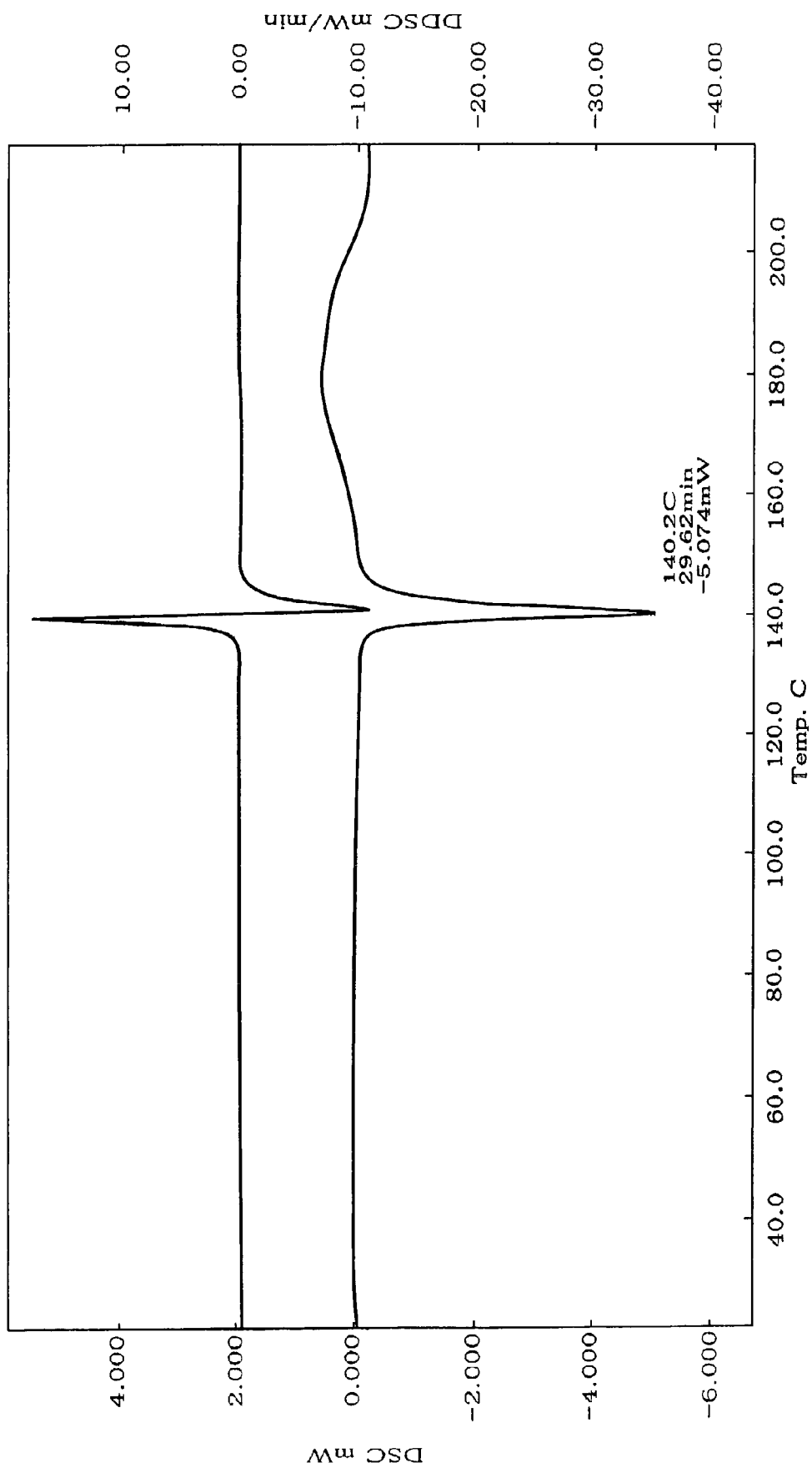
FIG. 3 shows a DSC pattern of H-type crystal form of a nateglinide drug substance.

The tablets produced in Example 2 were ground in an agate mortar and about 10 mg of the powder was placed in a silver pan and encapsulated by a silver lid. Then, DSC was measured by SII-DSC instrument under the condition wherein temperature was increased from 25° C. to 250° C. at a heating rate: 5° C./min. The results are shown in FIG. 1. They were compared with those of nateglinide drug substance powder in B-type form (FIG. 2) and those of nateglinide drug substance in H-type form (FIG. 3). As is apparent from FIG. 1 to FIG. 3, the tablets produced in Example 2 were confirmed to contain amorphous Nateglinide because they did not show absorption, which is characteristic of nateglinide crystals.

Figure 4:
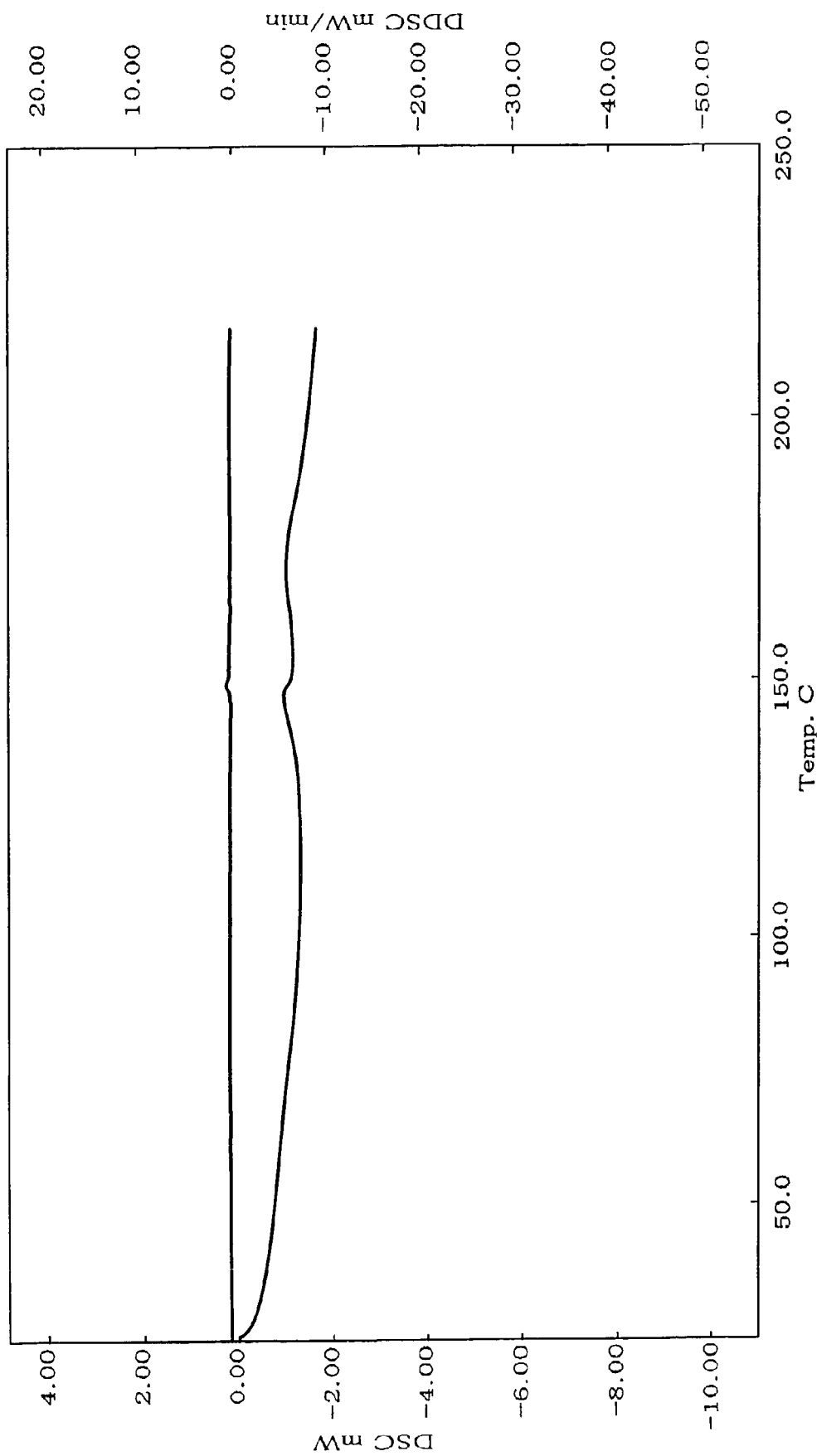
FIG. 4 shows a DSC pattern of amorphous nateglinide tablets after one week conservation packed in an aluminum bag at 50° C.
Figure 5:
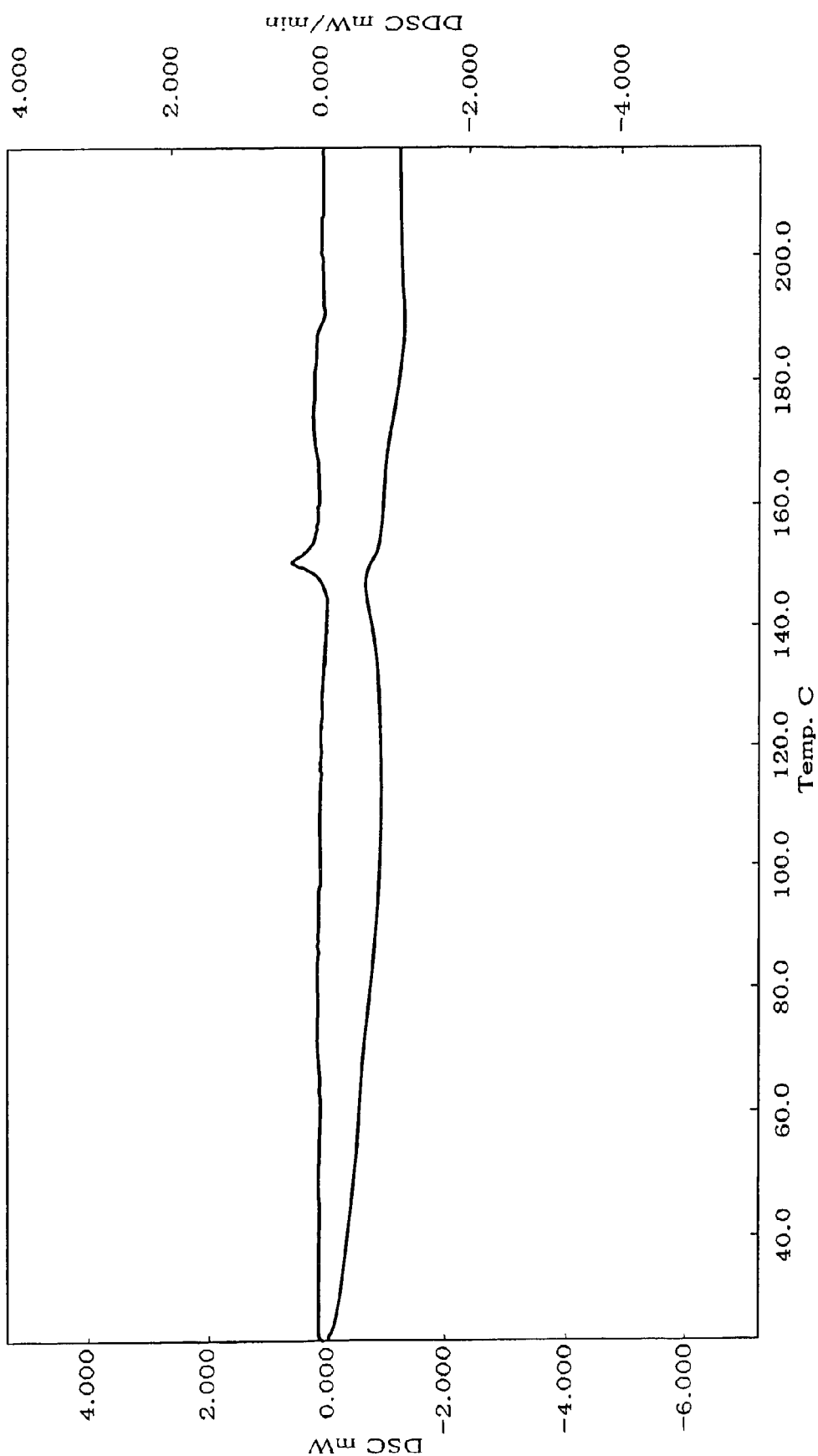
FIG. 5 shows a DSC pattern of amorphous nateglinide tablets after one month conservation packed in an aluminum bag at 40° C., 75% RH.

Meanwhile, a conservation tested sample of the preparations of Example 2 was measured by the same procedure mentioned above. The obtained DSC charts (FIG. 4 and FIG. 5) were the same as those obtained before a conservation test. Therefore, it was confirmed that nateglinide did not crystallize and was amorphous (no transition of crystal forms).

Example 5

Measurement of Dissolution Rate

Figure 6:
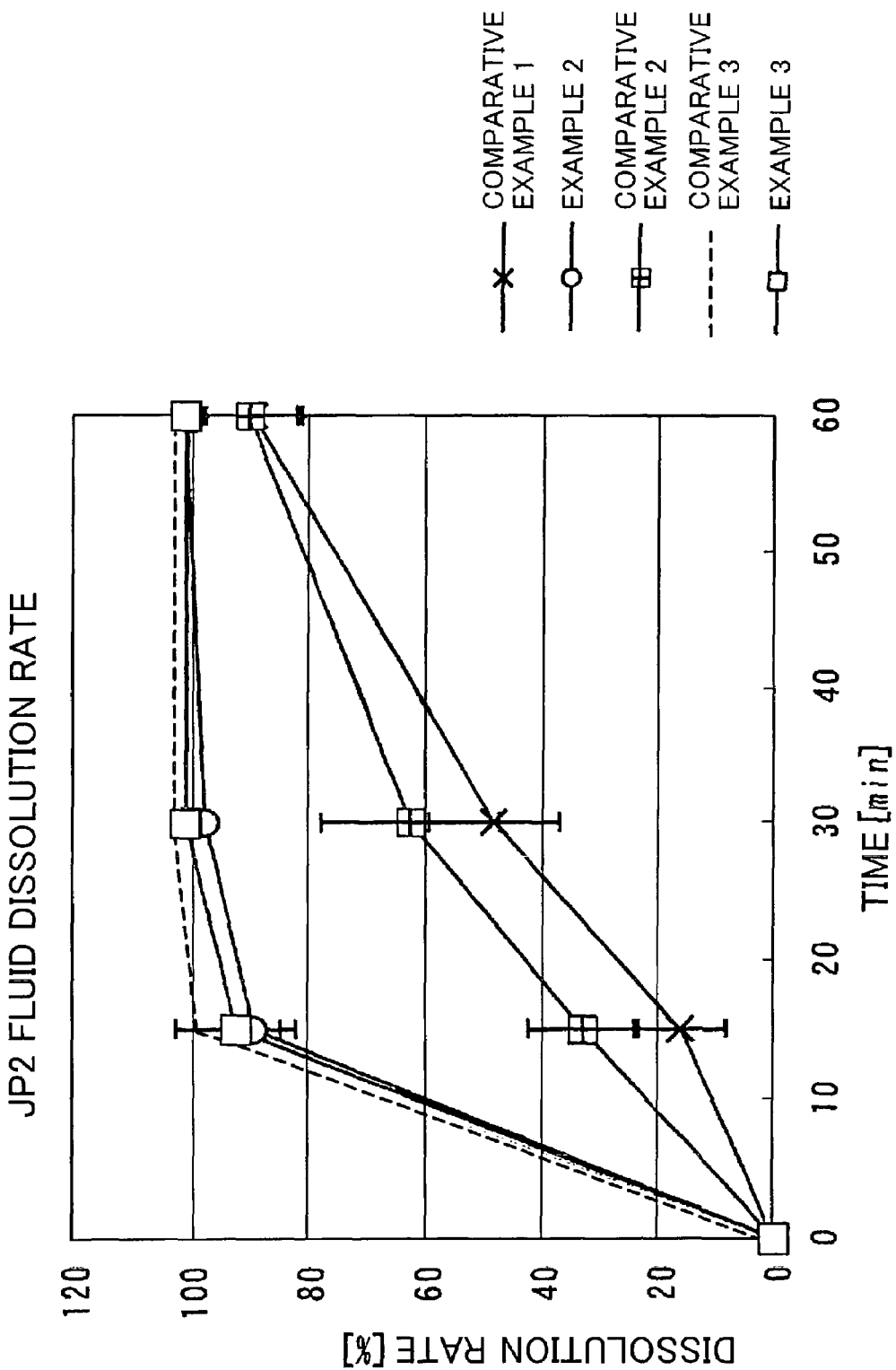
FIG. 6 shows a comparative diagram of dissolution profiles of each preparation of Examples 2 and 3 and Comparative Examples 1 to 3.

Dissolution property of the preparations produced in Example 2 and Example 3 was measured in 900 mL of the second fluid in Japanese Pharmacopoeia disintegration test in accordance with Japanese Pharmacopoeia (hereinafter referred to as JP), Chapter 13, a puddle method (50 rpm). The results are shown in FIG. 6. The preparations produced in Comparative Example 1 to Comparative Example 3 were measured by the same method mentioned above. The results are shown in FIG. 6.

As is apparent from FIG. 6, dissolution rates of the tablets produced in Example 2 and liquid-filled capsules produced in Example 3, wherein nateglinide were amorphous, are improved as compared with those of the capsules filled with drug substance powder produced in Comparative Example 1 and Comparative Example 2. The average dissolution rate of the tablets containing amorphous Nateglinide and liquid-filled capsules at each time point was confirmed as showing the same dissolution property as those of nateglinide tablets (tablets using H-type crystals) of Comparative Example 3.

Meanwhile, dissolution property of the preparations produced in Example 2 and of those after the conservation test were measured in 500 mL of the second fluid in Japanese Pharmacopoeia disintegration test in accordance with JP, Chapter 13, a puddle method (50 rpm, 30 minutes later). The results are shown in Table 1. As is apparent from Table 1, any change in the dissolution rate was not observed either before or after the conservation test.

TABLE 1

| Test samples | Before conservation | 50° C., one week later | 40° C., RH 75%, one month later |
|---|---|---|---|
| Dissolution rate % | 93 | 95 | 91 |

Example 6

Evaluation of Oral Absorbability on Beagles

Figure 7:
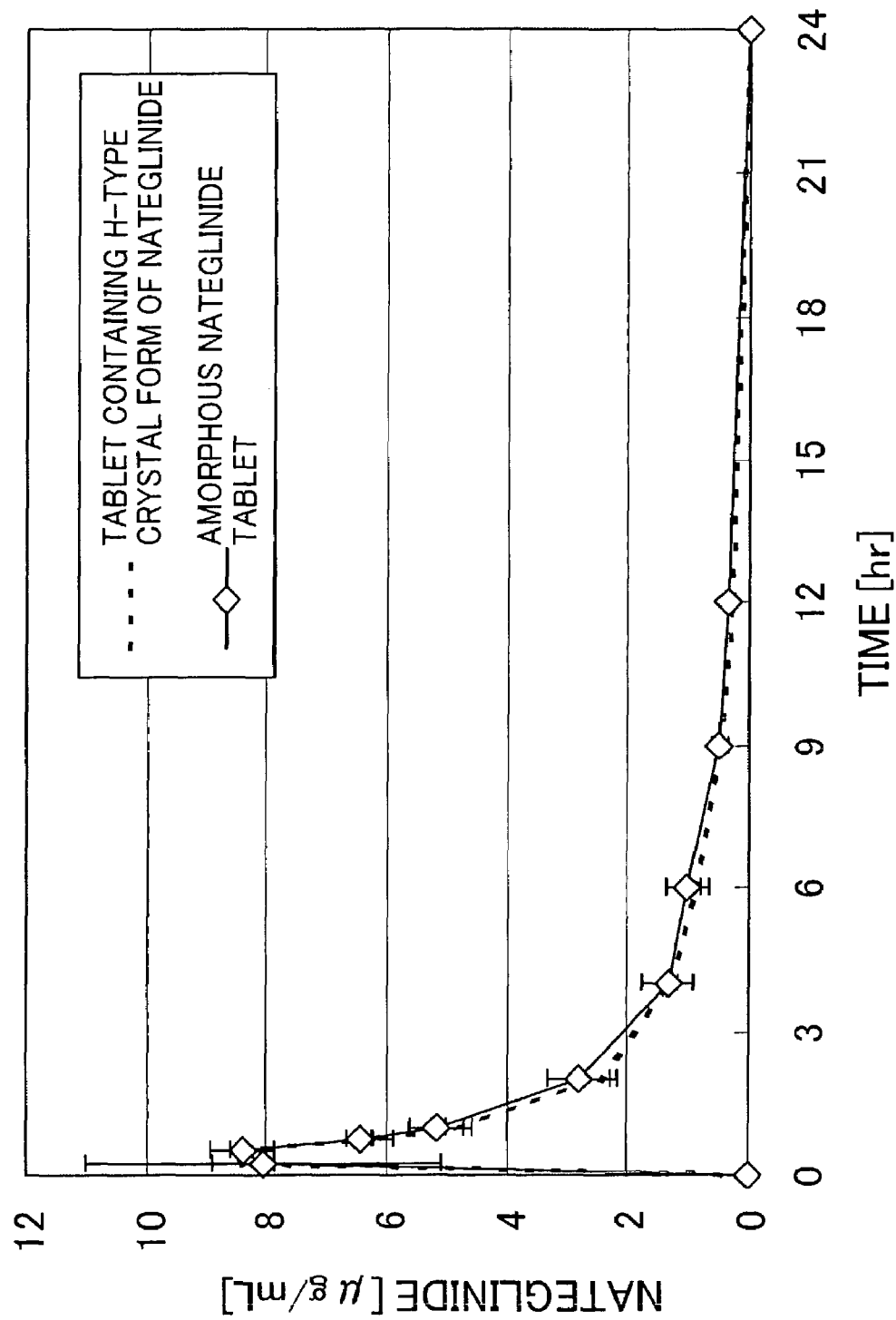
FIG. 7 shows a change in a nateglinide concentration in blood plasma when nateglinide tablets were administered to beagles five minutes before meal. Average±SE, n=3.
Figure 8:
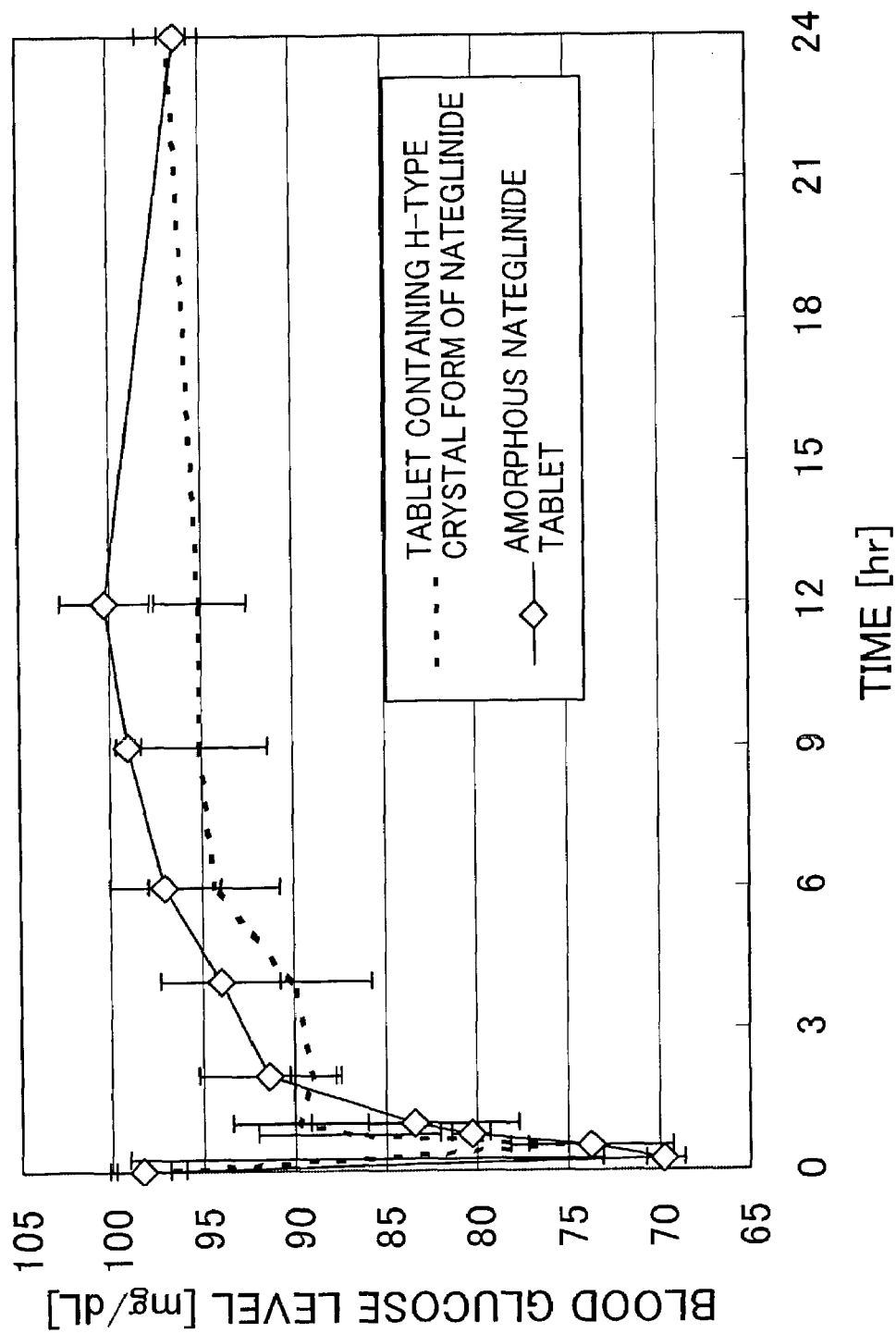
FIG. 8 shows a change in blood glucose level when nateglinide tablets were administered to beagles five minutes before meal. Average±SE, n=3.

A profile of a nateglinide concentration in blood plasma, a change in blood glucose level and a pharmacokinetic parameter were evaluated when amorphous nateglinide tablets obtained in Example 2 and nateglinide in H-type crystal form tablets obtained in Comparative Example 3 were administered to beagles five minutes before meal. The results are shown in FIG. 7, FIG. 8 and Table 2.

It was clarified that amorphous nateglinide tablets have equivalent or better oral absorbability and efficacy than those of nateglinide in H-type crystal form tablets.

TABLE 2

Pharmacokinetic parameter when nateglinide tablets were administered to beagles five minutes before meal (n = 3)

|  | AUC[μg/mL · hr] | Cmax[μg/mL] | Tmax[hr] |
|---|---|---|---|
| Nateglinide in H-type crystal form tablets | 20.53 | 8.93 | 0.38 |
| Amorphized nateglinide tablets | 22.29 | 9.46 | 0.38 |

Example 7

Evaluation of Conservation Stability of Amorphous Nateglinide Tablets

Figure 9:
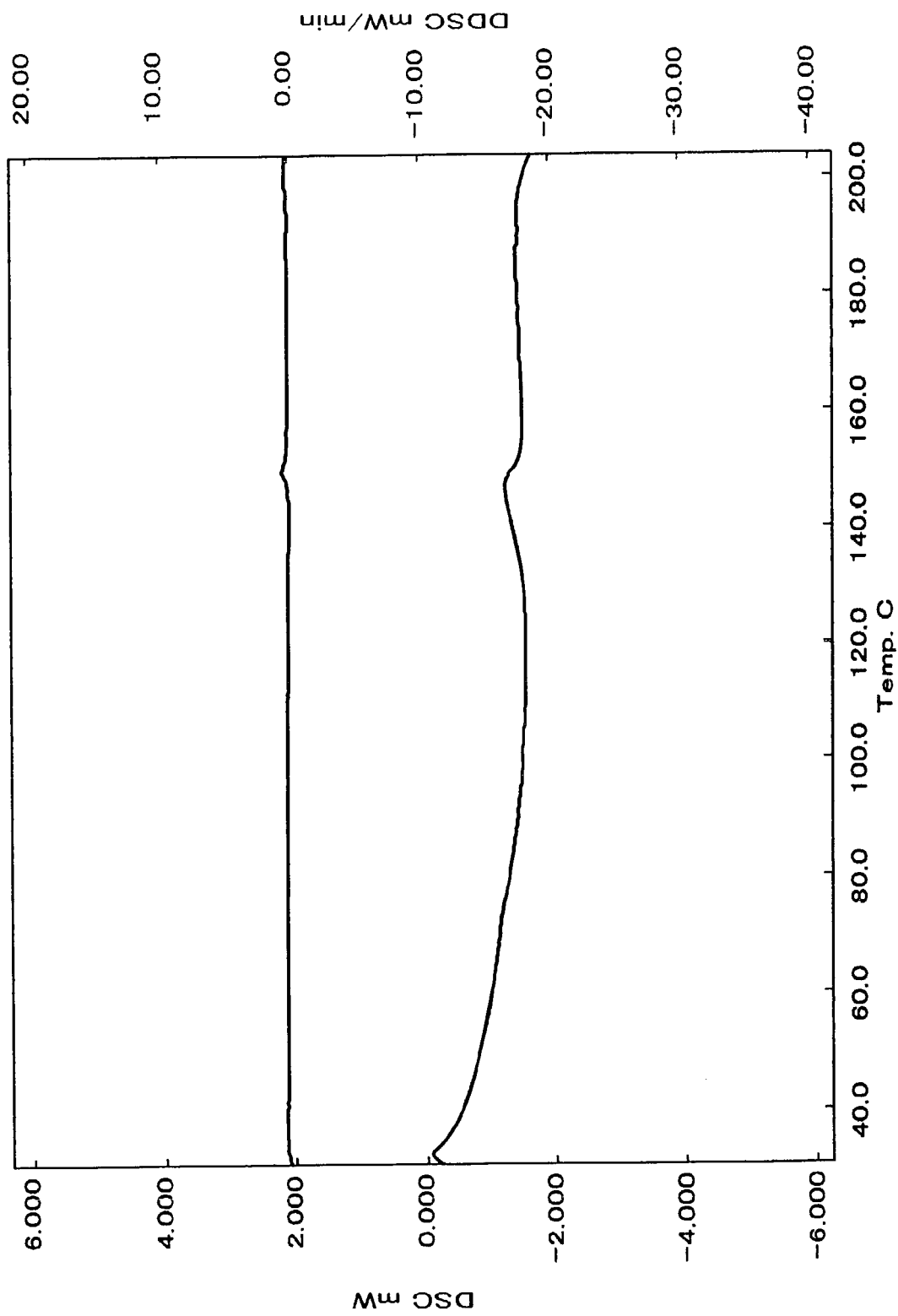
FIG. 9 shows a DSC pattern of amorphous nateglinide tablets after six month conservation packed in an aluminum bag at 40° C., 75%RH.

The amorphous nateglinide tablets obtained in Example 2 were packed in an aluminum bag and conserved at 40° C., 75%RH for six months. Dissolution property was evaluated in 500 mL of the second fluid in JP disintegration test in accordance with JP, Chapter 13, a puddle method (50 rpm, 30 minutes later). The results are shown in Table 3 and a DSC chart is shown in FIG. 9.

Any changes in dissolution rate and a DSC pattern were not observed either before or after the conservation. It indicates that amorphous nateglinide tablets are the preparation having high conservation stability.

TABLE 3

Comparison of solubility before and after the conservation

| Tablets | Dissolution Rate | |
|---|---|---|
| | Initial stage | 40° C., 75%, 6M |
| Amorphous nateglinide tablets | 93 (93-94) | 101 (99-104) |

It is apparent from each figure and Table 1 that amorphous nateglinide used in the preparation of the present invention does not transit to crystal forms during producing or conserving it. According to the present invention regarding the preparation using the amorphous nateglinide, while it contains nateglinide useful as an antidiabetic in the non-crystalline form, it is possible to produce preparations having high dissolution property equivalent to those containing crystalline nateglinide.

What is claimed is:

1. A method for producing an amorphous nateglinide-containing preparation, which comprises:
    mixing nateglinide crystals with at least one hydrophilic material selected from the group consisting of a water-soluble polymer, a water-swelling polymer, a sugar alcohol, a salt, and mixtures thereof, to obtain a mixture; and
    subjecting the resulting said mixture to melt-kneading with heating and grinding with cooling,
    wherein said water-soluble polymer or said water-swelling polymer is at least one member selected from the group consisting of a polyvinyl pyrrolidone compound, a polysaccharide, a polyacrylic acid compound, a polylactic acid compound, a polyoxyethylene compound, a polyvinyl alcohol compound, a surfactant, and mixtures thereof.

2. The method according to claim 1, wherein said hydrophilic material is a polysaccharide and said polysaccharide is at least one member selected from the group consisting of methylcellulose SM-4, hydroxypropylcellulose SL, hydroxypropylcellulose SSL, and mixtures thereof.

3. The method according to claim 1, wherein said hydrophilic material is a polyoxyethylene compound and said polyoxyethylene compound is polyethyleneglycol.

4. The method according to claim 1, wherein said hydrophilic material is a sugar alcohol and said sugar alcohol is at least one member selected from the group consisting of sorbitol, xylitol, mannitol, and mixtures thereof.

5. The method according to claim 1, wherein said hydrophilic material is a water-swelling polymer and said water-swelling polymer is crospovidone (KOLLIDON CL-M).

6. The method according to claim 1, wherein said melt-kneading is conducted in a heat-resistant multi-purpose mixer.

7. The method according to claim 1, wherein said hydrophilic material is at least a water-soluble polymer.

8. The method according to claim 1, wherein said hydrophilic material is at least a water-swelling polymer.

9. The method according to claim 1, wherein said hydrophilic material is at least a sugar alcohol.

10. The method according to claim 1, wherein said hydrophilic material is at least a salt.

11. The method according to claim 1, wherein said water-soluble polymer or said water-swelling polymer is at least a polyvinyl pyrrolidone compound.

12. The method according to claim 1, wherein said water-soluble polymer or said water-swelling polymer is at least a polysaccharide.

13. The method according to claim 1, wherein said water-soluble polymer or said water-swelling polymer is at least a polyacrylic acid compound.

14. The method according to claim 1, wherein said water-soluble polymer or said water-swelling polymer is at least a polylactic acid compound.

15. The method according to claim 1, wherein said water-soluble polymer or said water-swelling polymer is at least a polyoxyethylene compound.

16. The method according to claim 1, wherein said water-soluble polymer or said water-swelling polymer is at least a polyvinyl alcohol compound.

17. The method according to claim 1, wherein said water-soluble polymer or said water-swelling polymer is at least a surfactant.

18. The method according to claim 1, wherein said at least one hydrophilic material is a combination of hydroxypropyl cellulose and crospovidone.

19. The method according to claim 1, wherein said at least one hydrophilic material is a combination of a polysaccharide and a polyvinyl pyrrolidone.

20. The method according to claim 1, wherein said at least one hydrophilic material is a combination of a cellulose compound and a cross-linked polyvinyl pyrrolidone.

* * * * *